United States Patent
Mulzer et al.

(10) Patent No.: US 10,076,288 B2
(45) Date of Patent: Sep. 18, 2018

(54) MEDICAL TREATMENT OR EXAMINATION DEVICE

(71) Applicants: Harald Mulzer, Speinshart (DE); Wolfgang Neuber, Pressath (DE)

(72) Inventors: Harald Mulzer, Speinshart (DE); Wolfgang Neuber, Pressath (DE)

(73) Assignee: Siemens Aktiengesellschaft, München (DE)

( * ) Notice: Subject to any disclaimer, the term of this patent is extended or adjusted under 35 U.S.C. 154(b) by 439 days.

(21) Appl. No.: 14/272,723

(22) Filed: May 8, 2014

(65) Prior Publication Data

US 2014/0334608 A1   Nov. 13, 2014

(30) Foreign Application Priority Data

May 8, 2013  (DE) .......................... 10 2013 208 523

(51) Int. Cl.
*A61B 6/00* (2006.01)
*A61B 6/04* (2006.01)

(52) U.S. Cl.
CPC .............. *A61B 6/04* (2013.01); *A61B 6/44* (2013.01); *A61B 6/4441* (2013.01)

(58) Field of Classification Search
CPC ...................................................... A61B 6/04
See application file for complete search history.

(56) References Cited

U.S. PATENT DOCUMENTS 5,020,378 A * 6/1991 Hesthamer ............ G01L 3/102
                                                      324/209
5,230,112 A * 7/1993 Harrawood ............ A61G 13/02
                                                      5/607
7,117,752 B2 * 10/2006 May ........................ G01D 5/14
                                                      73/862.331

FOREIGN PATENT DOCUMENTS

| DE | 3871806 | 4/1993 |
| DE | 60309678 | 9/2007 |
| EP | 2399521 A1 | 12/2011 |
| WO | WO03016891 A2 | 2/2003 |

OTHER PUBLICATIONS

Chinese Office Action for related Chinese Application No. 2014 101 927 17.0 dated Mar. 3, 2017, with English Translation.
German Office Action dated Oct. 31, 2013 in corresponding German Patent Application No. DE 10 2013 208 523.0 with English translation.

* cited by examiner

*Primary Examiner* — Dani Fox
(74) *Attorney, Agent, or Firm* — Lempia Summerfield Katz LLC

(57) ABSTRACT

A medical treatment or examination device includes at least one device component that may move relative to at least one other device component via a drive device. A measuring device is provided for detecting a load acting on the movable device component. The measuring device includes a support that bends due to the load. The support, at least in a bending region, has a section producing a magnetic field. The measuring device also includes at least one coil that is assigned to the section and in which the magnetic field undergoing a change as a result of bending due to a load induces an induction current that serves as measurement signal describing the load.

17 Claims, 3 Drawing Sheets

MEDICAL TREATMENT OR EXAMINATION DEVICE

This application claims the benefit of DE 10 2013 208 523.0, filed on May 8, 2013, which is hereby incorporated by reference in its entirety.

BACKGROUND

The present embodiments relate to a medical treatment or examination device.

Very different treatment or examination devices are used in the medical setting. Many of these include device components that may move relative to one another. An example for this is an x-ray device including a patient bearing table, a tabletop of which may be adjusted vertically in terms of height using an appropriate drive device (e.g., the tabletop may move relative to the foot). By way of example, a different device component is a C-arm that supports the radiation source and the radiation receiver, arranged on a robot arm or the like. Using the robot arm, the C-arm may be moved in space. In this case, the C-arm may be moved relative to the adjoining robot-arm section. These are only a few examples for very different treatment or examination devices that find use in the medical field and have such movable device components.

A load is often applied to a movable device component. In the case of the patient bearing table described in an exemplary manner, this is the case when a patient is held on the tabletop. Depending on the patient mass, the load on the relevant components changes (e.g., in the region where the tabletop is fastened to the drive device that is to move the load). This may result in an influence on the moving processes such as displacement speed or reversal error in the movement axes. The load profile is also changed by changes in the load (e.g., when the patient is repositioned or repositions himself; the bend in the patient couch or table changes as a result of this and the like). Thus, the varying patient load is a variable and therefore influences the properties of such a treatment or examination device. Occasionally, there is also a load on such a device component when the device component is inadvertently moved against an obstacle (e.g., in the case of a movable C-arm). In this respect, use is made of complicated collision monitoring devices, mainly based on cameras, that attempt to avoid possible collisions in advance. However, collisions may not be ruled out completely. If a device component (e.g., the C-arm) impacts on an obstacle, a load is likewise applied thereon. If the load is sufficiently large, this may result in damage in the extreme case.

The patent document DE 38 71 806 T2 discloses a contactless measurement arrangement for tension in a rod-shaped body. In at least one transverse zone, the body is provided with a surface coating made of an amorphous magnetic material. Torsion of the body may be established with the aid of recording coils situated outside therefrom.

The patent document DE 603 09 678 T2 discloses a magnetic field sensor for detecting torque in a shaft.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a treatment or examination device that detects a load acting on a device component is provided.

In one embodiment, a treatment or examination device includes a measuring device for detecting a load acting on a movable device component. The measuring device includes a support. The support bends due to the load and, at least in the bending region, has a section producing a magnetic field. The measuring device also includes at least one coil that is assigned to the bending region and in which the magnetic field undergoing a change as a result of bending due to a load induces an induction current that serves as a measurement signal describing the load.

The treatment or examination device according to one or more of the present embodiments is distinguished by an integrated measuring device for detecting the load. This device is arranged or installed in a region that bends immediately when a load acts on a movable device component. This bending is detected, and the load is ultimately established from the degree of the bending or a value defining the load in more detail (e.g., a weight or force value is calculated). In order to render this possible, the measuring device has a support that bends due to the load. Thus, this support is installed such that the support bends under the action of a load. The support is embodied such that the support has a section that produces a magnetic field that, depending on the configuration of the support as solid material body or hollow body, only acts outward or acts outward and inward. This magnetic field or this section is situated in the bending region of the support (e.g., the region producing the magnetic field; is bent in the case of the load). This leads to a change in the magnetic field (e.g., the corresponding field vectors are also deformed since the field producing domains in the support material are displaced due to the bending).

At least one coil lying in the magnetic field is assigned to the magnetic field. If there is a field change or field distortion compared to the unloaded state as a result of the load, this change in the magnetic field leads to the induction of an induction current in the coil, even if the change is only small. This induction current is a measurement signal that is dependent on the degree of the magnetic field change. The degree of the magnetic field change is dependent on the degree of bending, which is dependent on the size of the load. Thus, the heavier a patient held on a patient tabletop is, the greater the bending is, and the greater the magnetic field change and, consequently, also the measurement signal are.

This measurement signal is read and processed by suitable processing or power electronics. The size of the load may be established very accurately from this measurement signal. Thus, in the case of a patient held on the bearing plate, the patient weight may be established very precisely. This provides that the patient may be weighed in the case where this was not possible prior to being laid on the bearing plate (e.g., because the patient cannot step onto scales or because the patient was repositioned from a couch to the patient couch, or the like). The drive device may be actuated appropriately depending on this information. Further information may be derived for operating the treatment or examination device by knowledge of this load (e.g., with respect to the radiation or medicament dose to be applied, and the like).

Similarly, if the load measuring device is, for example, assigned to the C-arm, possible collisions may be detected immediately since the measuring device is very sensitive. This is because even the smallest amount of bending leads to a field distortion, which results in a measurement signal. The measurement signal may be processed by the evaluation electronics, and a collision may thus be detected directly with the first contact. Hence, a load may be detected. Appropriate measures such as an immediate movement stop may then be taken up.

The magnetic field, which is generated in the bent bending region by the corresponding field generating section, is used for the virtually inverted magnetostrictive measurement principle. The magnetic field may be permanently magnetic (e.g., the support is treated prior to assembly such that a permanent magnetic field is impressed thereon). The support is to be made of a ferromagnetic material. Appropriate steels having, for example, a certain nickel and chromium proportion are suitable for this. In principle, use may be made of any steel on which a magnetic field with sufficient remanence may be impressed.

In one embodiment, the magnetic field is not impressed permanently, but is only impressed when a measurement is imminent. This may be possible if this relates to a targeted weight measurement. The support may be magnetized locally by applying current to the associated measurement coil, which, in the case of current being applied, produces a magnetic field that acts on the support. In this case, the magnetization is slightly lower (e.g., the field strength is slightly lower). However, this is not disadvantageous insofar as the field is not permanent but precisely only impressed when required. Also, there is no need to use support material allowing a permanent magnetic impression. Thus, if a short-term magnetic field is impressed by applying a current to the coil, the load measurement may directly adjoin this. The magnetic field then decays after a certain amount of time, but the magnetic field is sufficient for the simple load measurement. This field may also be impressed by a separately assigned impression coil and not by the measurement coil.

A permanent magnetic section may be embodied on the support. As described above, the permanent magnetic section may be impressed directly on the support. Alternatively, a permanent magnet that is securely fastened to and moves or slightly bends with the bending support may be arranged on the support. Therefore, a separate permanent magnet is fastened to the support for the purposes of producing the field. The permanent magnet is to be fastened such that the permanent magnet joins in with any support movement such that the field change occurs.

The support may be a hollow shaft, within or outside of which the at least one magnetic coil is arranged. Depending on the given spatial conditions, the measurement coil may consequently be positioned in the interior of the hollow shaft in the region of the magnetic field there, or outside of the hollow shaft in the region of the magnetic field. The corresponding positioning is possible since the corresponding measurement coil is arranged on a corresponding coil holder that is arranged relative to the shaft.

The coil holder, which may be a simple plastic component, offers the option of fixing the at least one coil and positioning the at least one coil relative to the support. The coil may be placed on the coil holder. In one embodiment, the coil may be encapsulated in the coil holder (e.g., consequently, to cast the coil or the like). The magnetic field is not influenced by the coil holder material (e.g., neither distorted nor attenuated), such that any field change is immediately registered on the part of the coil.

In a development, two coils that form a pair and are arranged in a row, both axially and in a manner aligned with one another, are provided. Therefore, a coil pair is used in accordance with one or more of the present embodiments. Each coil supplies its own measurement signal. Common mode rejection by a differential measurement may thus be realized. As a result, effects caused by possible external magnetic fields may be compensated for. The coils are to be arranged in a row, both exactly and in a manner aligned with one another, and the coils are to be matched accordingly.

In one embodiment, a plurality of coils (e.g., a plurality of coil pairs) is provided. Each coil of the plurality of coils supplies a separate measurement signal. The plurality of coils are positioned in an opposite or circular arrangement (e.g., in the interior of the hollow shaft or around the hollow shaft). If only directional bending may be provided (e.g., in the case of a patient bearing plate), it is sufficient to provide only one or two coils or coil pairs lying opposite one another. These are arranged vertically above one another. The coils or coil pairs may experience the same field distortion and supply comparable signals such that there is a certain amount of redundancy. In the case of an undirected load introduction, there consequently is an arbitrary bending direction. If in this case a plurality of coils or coil pairs are arranged in a circular form, the corresponding bend and hence the load may be detected equally precisely since different measurement signals are also available from the different coils or coil pairs. The measurement signals may be correspondingly interpolated or processed in any other way.

If a plurality of coils are arranged in the interior of the shaft, the plurality of coils may be positioned around a soft-magnetic core. This soft magnetic core serves for the field amplification and, therefore, for the signal amplification.

As described above, an actuation of the support with the load that is as direct as possible may be provided. This is why the support may directly connect the device component to which the load is applied to the other device component. In one embodiment, the support may be arranged on a third device component if the load is transferred accordingly and the bending load occurs on the subsequently positioned point. An example for this would be a horizontally pivoted C-arm, which is pivoted by a robot arm. The measuring device may be arranged, for example, in the region of a subsequent joint receiving a transverse load in the process. Consequently, the support or the measuring device is positioned depending on the design of the treatment or examination device, or depending on the measurement object to be processed.

The device component, to which the support is connected, may be a drive device (e.g., a lifting device with a corresponding linear guide). However, other drive devices such as, for example, drives for the C-arm movement, either along the arm or in the region of robot arm joints or the like, may also be provided as connection points for the support.

DETAILED DESCRIPTION

Figure 1:
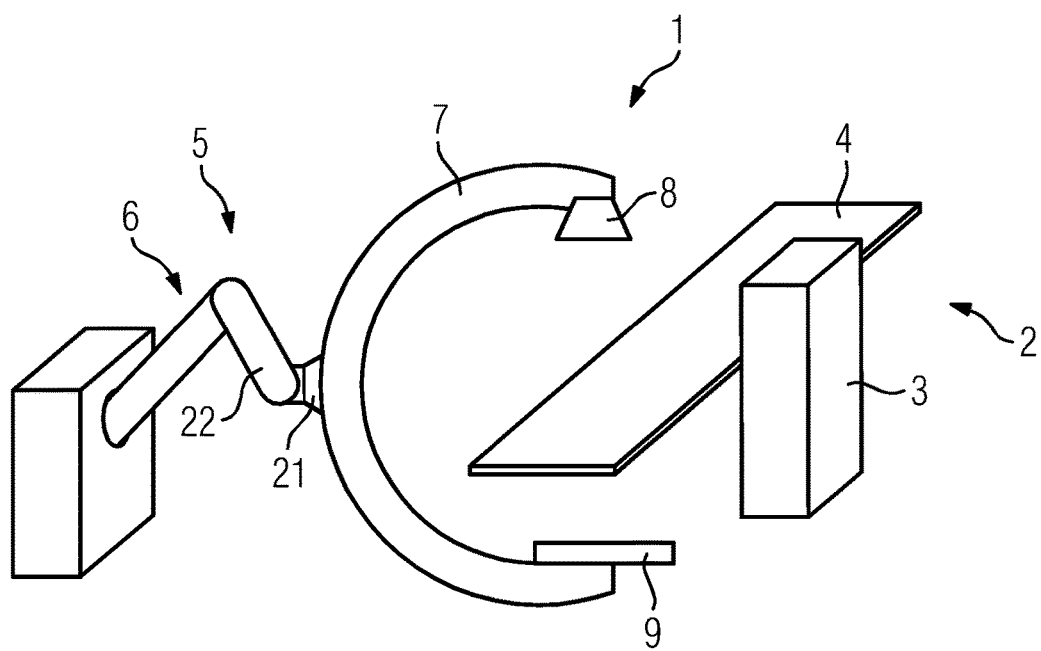
FIG. 1 shows one embodiment of a medical treatment or examination device.

FIG. 1 shows one embodiment of a medical treatment or examination device 1. The medical treatment or examination device includes a patient bearing table 2 including a foot 3 with an integrated lifting device and a patient bearing tabletop 4 that is arranged on the foot 3 or the lifting device and may be moved vertically by the lifting device. The medical treatment or examination device includes an image recording device 5. The image recording device 5 includes a C-arm 7 arranged on a robot arm 6. A radiation source 8 and a radiation receiver 9 are arranged on the C-arm 7. The C-arm 7 may be moved freely in space using the robot arm 6. Consequently, the C-arm 7 may also be moved relative to the patient couch 2 and therefore relative to a patient situated thereon.

In order to undertake a measurement of the patient weight or a given patient load on the patient couch 2 and/or to realize a collision detection option on the robot arm 6 or the C-arm 7 so as to detect a possible collision with another object, an appropriate load measuring device is provided. The load measuring device is shown in a first embodiment in FIGS. 2 and 3. The measuring device 9 may be arranged in the connection region between the patient bearing tabletop 4 and a component 10 of the drive device (e.g., the lifting device) that may be moved vertically (e.g., using an appropriate spindle mechanism or the like). The patient bearing tabletop 4 may then be moved using the vertical motion.

The measuring device includes a support 11 (e.g., in the form of a hollow shaft 12 including a ferromagnetic material). A permanent magnetic region is impressed onto the shaft 12 in one section 13. This permanent magnetic region produces a magnetic field 14 that extends both in the interior and exterior of the shaft 12 and is indicated by the dashed circular line. The magnetic field 14 has defined field vectors (e.g., the magnetic field 14 has a defined profile that is given in the load-free state). As shown, a clearance 23 is provided on the shaft 12. The clearance defines the bending region (e.g., where the bending is initiated). Therefore, a defined bending zone is realized over this clearance 23.

The measuring device 9 also includes at least one coil 15 (e.g., a plurality in the depicted example) that is arranged secured in position on a common coil holder 16 made of, for example, plastic. The coils 15 have a helical winding and extend in the longitudinal direction of the shaft 12. The coil holder 16 is arranged, secured in position in the interior of the hollow shaft 12 in a suitable manner, such that the shaft 12 may move (e.g., relative to the coil holder 16 and therefore also relative to the coils 15). A soft magnetic core 17 serving for signal amplification is arranged in the interior of the coil arrangement. This will be discussed in more detail below. Seen radially, the coils 15 lie in a region 13 (e.g., in the magnetic field 14).

If a load (e.g., a patient) is applied on the patient bearing table 4, as indicated by the arrow P, there is also a load on the shaft 12 that, as described, constitutes the connection between the patient bearing table 4 and the device component 10 of the drive device, or is at least arranged in this region. The shaft 12 bends since the device component 10 is fixedly arranged on the foot side or is guided by a stable linear guide. The shaft 12 is therefore bent slightly downward, following the load (arrow P), on the left-hand side in the depicted example. This bending is relatively small. There still is an elastic deformation of the shaft 12 and hence also of the section 13 in which the permanent magnetization is provided. This leads to the generated magnetic field 14 being modified and locally distorted. There is a shift in the field vectors due to the bending. The greater the load is, the stronger the bending and, consequently, the elastic deformation of the shaft 12 and, resulting therefrom, also the change in the field are.

Since the coils 15 are situated in the magnetic field 14, the change in field (e.g., the field movement) leads to an induction of an induction current in the coils 15. This induction current is provided to evaluation electronics 19 via appropriate line connections 18. The evaluation electronics 19 include the measurement signals (e.g., low measurement signals; the induction currents). Since the signal level or strength is dependent on the size of the load, appropriate calibration makes it possible to establish precisely the size of the load and hence the weight of the patient from the given measurement signal).

If the load is once again removed from the patient bearing tabletop 4, the shaft 12 returns to a non-deformed original position, and the impressed permanent magnetic field returns to the calibrated initial state.

Figure 3:
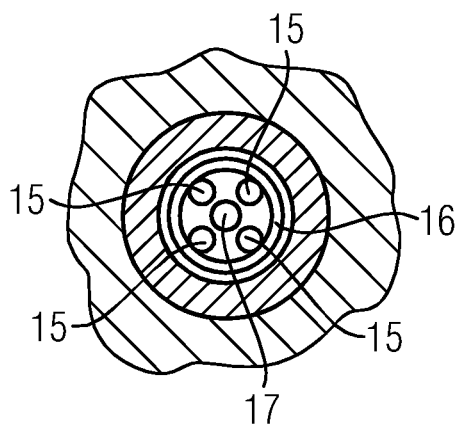
FIG. 3 shows an end view in the direction of the line III in FIG. 2.

As shown in FIG. 3, four helically wound coils 15 are arranged on the coil holder 16 and symmetrically distributed around the core 17 in the depicted example. More than four of such coils 15 may be provided. Such a circular arrangement is advantageous in that slightly undirected loads may also be detected (e.g., in the case where the patient bearing tabletop 4 may also be slightly pivoted about a horizontal axis such that the plate is no longer arranged horizontally).

Figure 2:
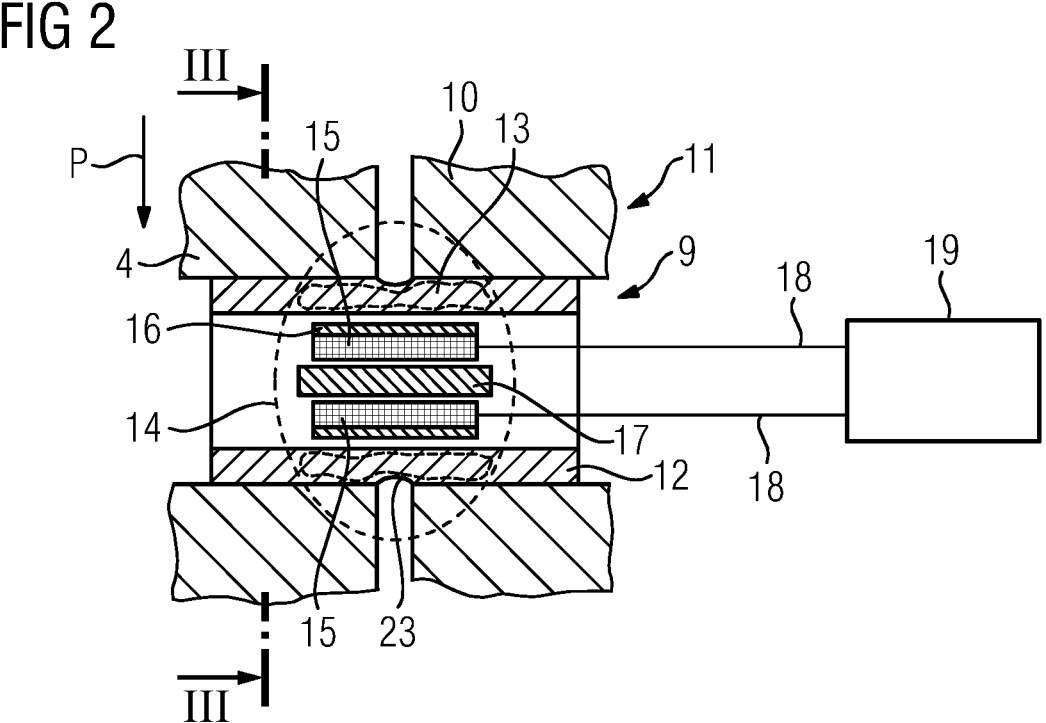
FIG. 2 shows a measuring device for detecting a load in a first embodiment.
Figure 4:
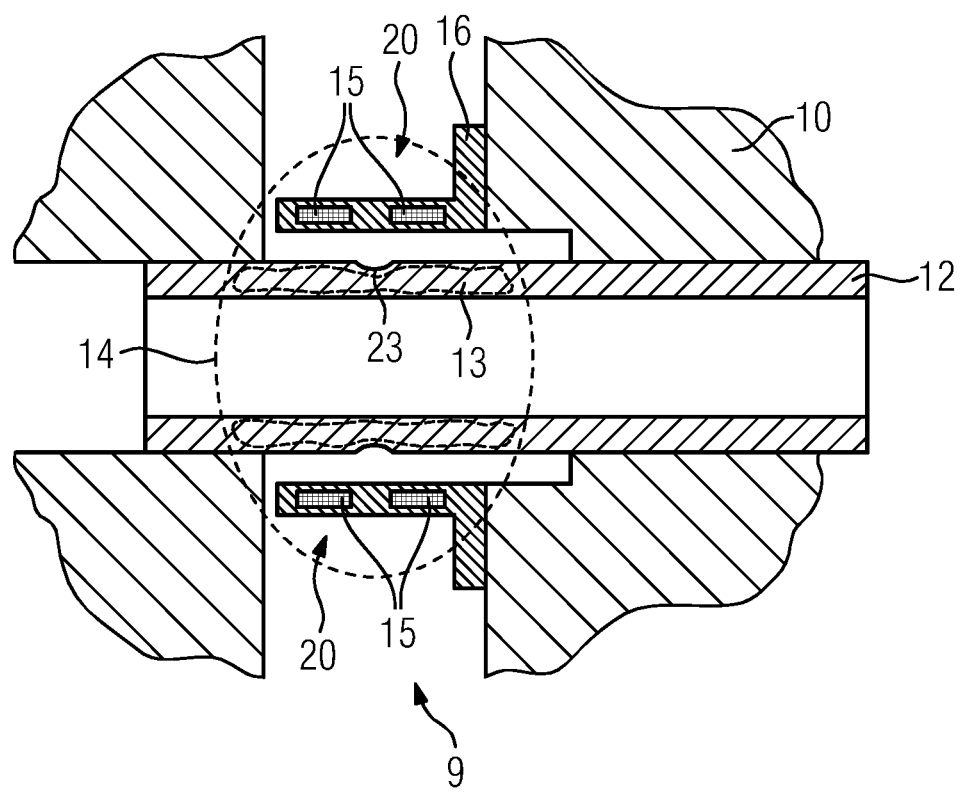
FIG. 4 shows a measuring device in a second embodiment.

FIG. 4 shows an embodiment of a measuring device 9 that is based on the same operational principle as the measuring device 9 described in FIGS. 2 and 3. The measuring device 9 includes a hollow ferromagnetic shaft 12 with a section 13 that carries permanent magnetization. This permanent magnetization produces a magnetic field 14 (dashed circular line) that is provided within and outside of the shaft 12.

In this configuration, the coil holder 16 is arranged outside of the shaft 12 on the device component 10. The arrangement only allows the shaft 12 to deform relative to the coil holder 16 (e.g., the coil holder 16 is rigid). In this case, a hollow cylindrical embodiment may be provided, and thus, the shaft 12 passes therethrough. In the depicted exemplary embodiment, two coil pairs 20, each including two helically wound coils 15, are provided on the coil holder 16. The respective coils 15 are, as seen axially, arranged in a row in a manner aligned with one another. As seen radially, the respective coils 15 are arranged in the region 13 (e.g., in the magnetic field 14). Each coil 15 of a coil pair supplies its own measurement signal, and two measurement signals are thus provided by each coil pair 20. This enables a differential measurement. As a result of the differential measurement, common mode rejection and hence the compensation of external magnetic field influences, provided these exist, may be provided.

Even though, in principle, it is sufficient to provide only one coil pair 20, at least a second coil pair 20 lying opposite one another may be provided. Each coil pair when loaded as a result of the field change experiences the same influence. In one embodiment, the coil pair-side measurement signals are the same. The second coil pair 20 is consequently provided for reasons of redundancy. However, the second coil pair 20 may also be used for precise detection of an average signal or the like, depending on how the evaluation electronics 19 are designed with respect to processing the measurement signals.

The distance between the coils 15 and the shaft 12 may be as small as possible so that the signal-to-noise ratio is as low as possible. The distance is, however, to be sufficiently large so that there is no contact when the shaft 12 bends. As explained above, the bending of the shaft is only very small as a result of the stable design of the appropriate connections. The measuring device 9 enables highly precise and very fine load detection.

While the exemplary embodiments in accordance with FIGS. 2-4 describe the integration of the measuring device 9 in the coupling region of the patient bearing tabletop 4 and lifting device in an exemplary manner, such a measuring device 9 may also be arranged in the region of the robot arm 6 (e.g., in the region in which the C-arm 7 is arranged on a corresponding holder 21, along which the C-arm 7 may be displaced around an arm length of the C-arm 7, or on which the C-arm 7 is arranged rotatably about an axis). The measuring device 9 may provide for collision detection. This is because if the C-arm is driven against an obstacle, the result is a load on the connection of the C-arm on the holder 21 or the following robot arm section 22 in this region. This load leads to a corresponding bending or torsion of the corresponding shaft 12, which is arranged in this region, and a possible collision case may be detected immediately. Appropriate measures may then be initiated. The measuring device 9 may detect both pure bending and torsion (e.g., a torque). The alignment of the individual coils 12 (e.g., helically wound coils) may be set appropriately relative to the magnetic field (e.g., consequently align the individual coils 12 either along or across the shaft longitudinal axis).

Even though the invention was illustrated by the exemplary embodiments, the invention is not restricted by the disclosed examples. Other variations may be derived herefrom by a person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical treatment or examination device comprising:
   a patient bearing table having a table top and a table foot on which the table top is mounted, wherein the table top is movable relative to the table foot via a drive device;
   a measuring device connecting the table top and the drive device, wherein the measuring device is operable to detect a load acting on the table top, the measuring device comprising:
      a ferromagnetic support operable to bend due to the load, the ferromagnetic support including a section operable to produce, at least in a bending region, a magnetic field; and
      a coil that is assigned to the section of the ferromagnetic support, wherein the coil is configured to induce an induction current based on a change in the magnetic field as a result of bending due to the load, wherein the induction current serves as a measurement signal describing the load.

2. The medical treatment or examination device of claim 1, wherein the section is permanently magnetic.

3. The medical treatment or examination device of claim 2, wherein the permanently magnetic section is disposed on the ferromagnetic support, or a permanent magnet is arranged on the ferromagnetic support, the permanent magnet being securely fastened to and moving with the bending region of the ferromagnetic support.

4. The medical treatment or examination device of claim 1, wherein the ferromagnetic support is a hollow shaft, the coil being arranged within or outside of the hollow shaft.

5. The medical treatment or examination device of claim 4, wherein the coil is arranged on a coil holder.

6. The medical treatment or examination device of claim 1, wherein the coil is a first coil, and the medical treatment or examination device further comprises a second coil, and
   wherein the first coil and the second coil form a pair of coils and are arranged in a row, both axially and in a manner aligned with one another.

7. The medical treatment or examination device of claim 4, wherein the coil is a first coil of a plurality of coils, each coil of the plurality of coils operable to supply a separate measurement signal.

8. The medical treatment or examination device of claim 7, wherein the plurality of coils or coil pairs of the plurality of coils are arranged in an interior of the hollow shaft and are arranged around a soft-magnetic core.

9. The medical treatment or examination device of claim 1,
   wherein the table top is mounted in a vertically movable manner.

10. The medical treatment or examination device of claim 3, wherein the ferromagnetic support is a hollow shaft, the coil being arranged within or outside of the hollow shaft.

11. The medical treatment or examination device of claim 10, wherein the coil is arranged on a coil holder.

12. The medical treatment or examination device of claim 11, wherein the coil is a first coil, and the medical treatment or examination device further comprises a second coil, and
   wherein the first coil and the second coil form a pair of coils and are arranged in a row, both axially and in a manner aligned with one another.

13. The medical treatment or examination device of claim 3, wherein the coil is a first coil, and the medical treatment or examination device further comprises a second coil, and
   wherein the first coil and the second coil form a pair of coils and are arranged in a row, both axially and in a manner aligned with one another.

14. The medical treatment or examination device of claim 3, wherein the coil is a first coil of a plurality of coils, each coil of the plurality of coils operable to supply a separate measurement signal.

15. The medical treatment or examination device of claim 5, wherein the coil is a first coil of a plurality of coils, each coil of the plurality of coils operable to supply a separate measurement signal.

16. The medical treatment or examination device of claim 15, wherein the plurality of coils or coil pairs of the plurality of coils are arranged in an interior of the hollow shaft and are arranged around a soft-magnetic core.

17. A medical treatment or examination device comprising:
   a patient bearing table having a table top and a device component on which the table top is mounted, wherein the table top is movable relative to the device component via a drive device;
   a measuring device connecting the table top and the drive device, wherein the measuring device is operable to detect a load acting on the table top, the measuring device comprising:

a hollow support operable to bend due to the load, the hollow support including a section operable to produce, at least in a bending region, a magnetic field; and a plurality of coils assigned to the section of the hollow support, wherein the coil is configured to induce an induction current based on a change in the magnetic field as a result of bending due to the load, wherein the induction current serves as a measurement signal describing the load, wherein the plurality of coils is arranged in an interior of the hollow support and around a soft-magnetic core.

* * * * *